United States Patent [19]

Woessner

[11] 4,206,127
[45] Jun. 3, 1980

[54] 5,6-DIHYDRO ANALOGUES OF PROSTAGLANDIN I$_2$

[75] Inventor: Warren D. Woessner, Madison, Wis.

[73] Assignee: Miles Laboratories, Inc., Elkhart, Ind.

[21] Appl. No.: 949,401

[22] Filed: Oct. 12, 1978

Related U.S. Application Data

[63] Continuation-in-part of Ser. No. 854,338, Nov. 23, 1977, abandoned.

[51] Int. Cl.$^2$ .................. C07D 311/94; C07D 307/93
[52] U.S. Cl. ........................... 260/345.2; 260/346.22; 424/283; 424/285; 542/422
[58] Field of Search ...................... 260/345.2

[56] References Cited

U.S. PATENT DOCUMENTS 4,123,441  10/1978  Johnson ........................... 260/345.2

Primary Examiner—Robert Gerstl
Attorney, Agent, or Firm—Jerome L. Jeffers

[57] ABSTRACT

Derivatives of prostaglandin I$_2$ characterized by the generic structural formulae,

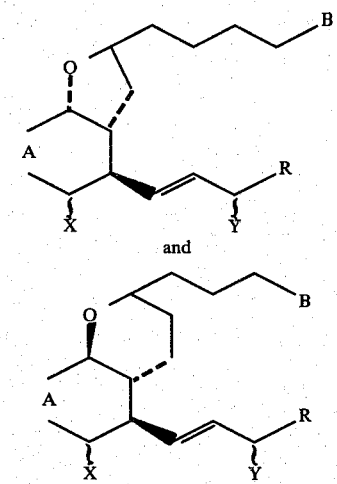

and are useful for inhibiting platelet aggregation or gastric acidity in individuals for whom such therapy is indicated. In the preceding structural formulae: B is CH$_2$OH or COOT, where T is hydrogen, an alkyl group having from 1-3 carbon atoms or a pharmacologically acceptable cation; X and Y are hydrogen or a hydroxyl group; A is methylene or ethylene; and R is a pentyl, cyclohexyl, bicyclo[3.2.0]-hept-3-yl or 1,1-dimethylpentyl group.

6 Claims, No Drawings

5,6-DIHYDRO ANALOGUES OF PROSTAGLANDIN I₂

BACKGROUND AND PRIOR ART

This application is a continuation-in-part of co-pending application Ser. No. 854,338 filed on Nov. 23, 1977, now abandoned.

Prostaglandin I₂, I (PGX, PGI₂, prostacyclin, (5Z)-9-deoxy-6,9α-epoxy-Δ⁵-prostaglandin F₁α),

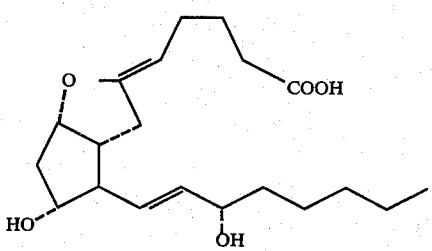

is a newly discovered prostaglandin reported by scientists at the Conference on Prostaglandins and Thromboxanes, Santa Monica, California on Dec. 3, 1976. (C&EN, Dec. 20, 1976, p. 17). It appears to play a key role in platelet aggregation. PGI₂ also acts to inhibit platelet aggregation and is the most potent inhibitor of platelet clumping of all the prostaglandins discovered to date. PGI₂ also destroys platelet clumps after they have been induced to form (in vitro). In addition PGI₂ dilates blood vessels dramatically.

The structure of I has been confirmed by synthesis by Corey et al. (J. Amer. Chem. Soc., 99: 2006, 1977).

Earlier, evidence for I in the biosynthetic conversion of arachidonic acid into prostaglandins by rat stomach homogenates had been obtained by Pace-Asciak and Wolfe (Biochemistry, 10: 3657, 1971).

Pace-Asciak and Wolfe also reported the compound

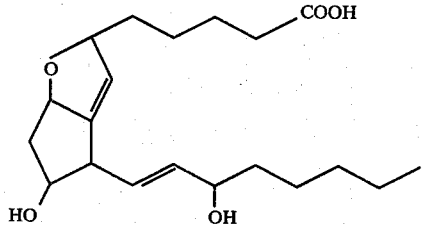

an isomer of PGI₂, having the double bond at position C₇-C₈, within the ring, rather than exo to the ring as in PGI₂. No utility was reported for this compound. They also reported compound III,

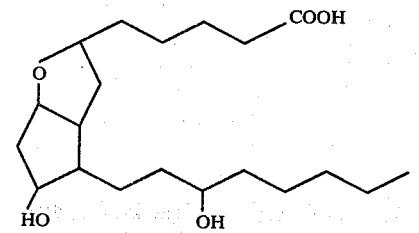

which was isolated after catalytic hydrogenation of the chromatographically separated fraction containing I and II. Again no utility or pharmacological activity was reported or suggested. This prior art thus provides no structure-activity relationships that suggest that hydrogenated PGI₂ derivatives may have platelet aggregation inhibiting or gastic anti-secretory properties.

Corey, et al. (J. Amer. Chem. Soc., 99: 2006 [1977], published Mar. 16, 1977) also reported the synthesis of compound IV,

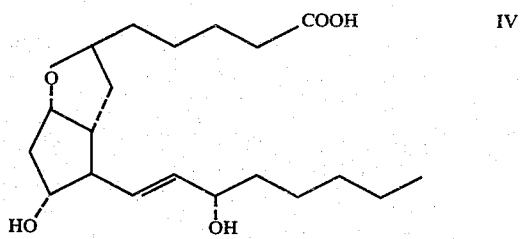

the subject of this invention, by a process similar to that disclosed herein.

Udo Axen described 5,6-dihydro PGI₂ (IV) on March 23 1977 at the 193rd National Meeting of the American Chemical Society in New Orleans, Louisiana.

SUMMARY OF THE INVENTION

The subject matter of this invention includes
(1) pharmacologically active novel dihydro derivatives of prostaglandin I₂; and
(2) a method of preparing such derivatives.

DETAILED DESCRIPTION OF THE INVENTION

The derivatives of prostaglandin I₂ that are part of the subject matter of this invention include compounds characterized by the general structural formulae,

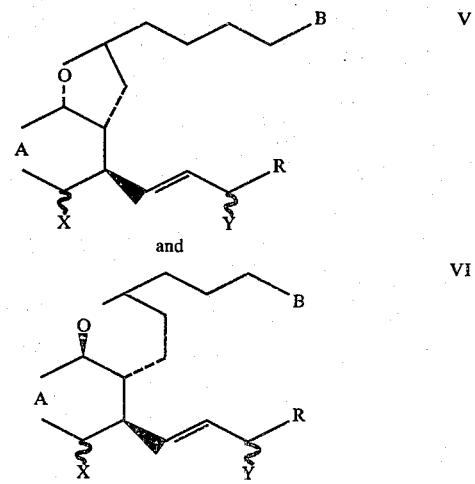

In V and VI, as well as in any subsequent formula, B is selected from the class consisting of $CH_2OH$ or $COOT$, where T is hydrogen, an alkyl group possessing from 1 to 3 carbon atoms or a pharmacologically acceptable cation; X and Y are selected from the class consisting of hydrogen or hydroxyl; A is methylene or ethylene; R is pentyl, cyclohexyl, bicyclo[3.2.0]hept-3-yl or 1,1-dimethylpentyl; the wavy line (∼) indicates groups that may be either above or below the plane of the paper as written; and as used herein, the dotted line (---) indicates groups projecting below the plane of the paper as written and the wedged line (▶) indicates groups projecting above the plane of the paper as written.

Compounds V and VI are useful as platelet aggregation inhibitors and as gastric antisecretory agents. Example 18 provides details of such utility in experimental protocols recognized in the art.

The method of preparing compounds V and VI proceeds via the synthesis diagrammed in Table A and described below.

from 1 to 3 carbon atoms; A is methylene or ethylene; Z and Z', either the same or different, are selected from the class consisting of hydrogen or a hydroxyl group protected with an acid labile protecting group. The reaction mixture is cooled to a temperature of from $-30°$ C. to $0°$ C. The cooled mixture is then treated with a borohydride reducing agent in the presence of water or alcohol for a period of from 0.25 to 4 hours to yield the intermediate compounds VIII or X, respec-

TABLE A

Synthetic Pathway for the Preparation of Compounds V and VI

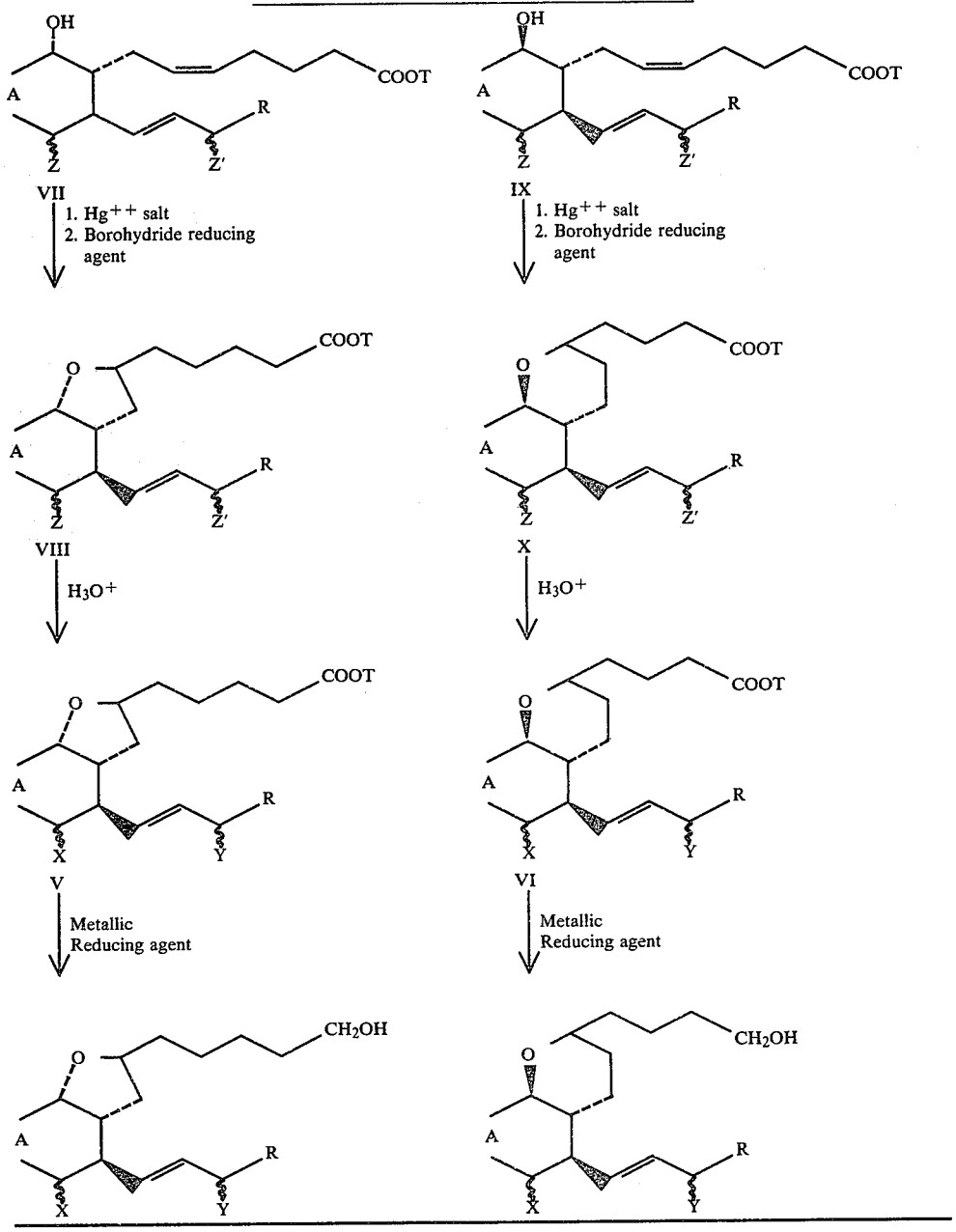

An appropriate first starting material consisting of a PGF$_{2\alpha}$ or PGF$_{2\beta}$ ester or acid or a hydroxyl-protected PGF$_{2\alpha}$ or PGF$_{2\beta}$ ester or acid (VII or IX, respectively) is first reacted with a mercury salt in a polar organic solvent for 1–72 hours at a temperature from $10°$ C. to $40°$ C.; where T is hydrogen or an alkyl group having tively. Subsequent treatment of the intermediates (VIII or X), when Z or Z' are hydroxyl groups protected with acid-labile hydroxyl-protecting groups, with a mild acid removes the acid-labile hydroxyl-protecting group to give the ester or acid products of compounds V and VI respectively where B is CO₂T. It should be noted that the acid or acid salt of compounds V and VI also may be produced from the corresponding ester by well-known reactions such as treatment with a base. Further reduction of these ester or acid products with a metallic reducing agent in a polar aprotic solvent such as ether, benzene and the like gives the corresponding carbinol product V and VI respectively where B is CH₂OH. The acid and ester products are preferably isolated from the reaction mixture before reduction to the corresponding carbinol products. A procedure similar to the conversion of VII to VIII and IX to X has been utilized to identify mono-enoic long chain alcohols (Gunstone and Inglis, *Chem. Commun.*, 12 [1972]).

Preferred modes of the method described above involve substitution of a first starting material having a formula selected from the following:

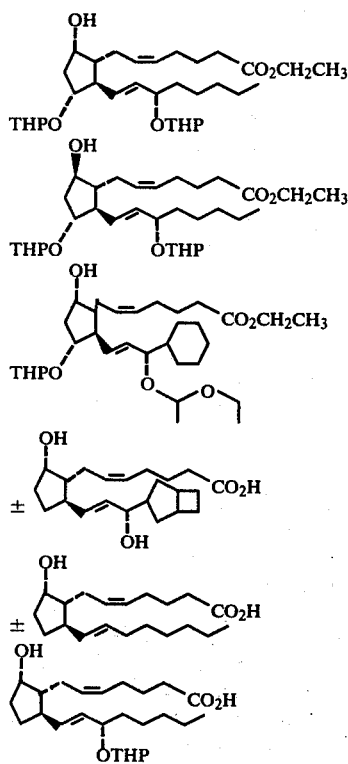

VII-a;

VII-b;

VII-c;

VII-d;

VII-e;

for structures VII and IX respectively. Such preferred mode of the method provides the corresponding products having a formula selected from the following:

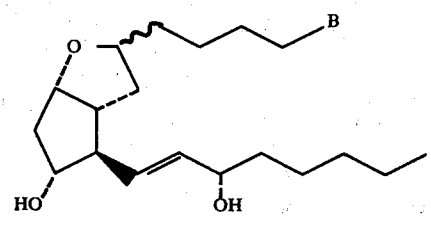

V-a;

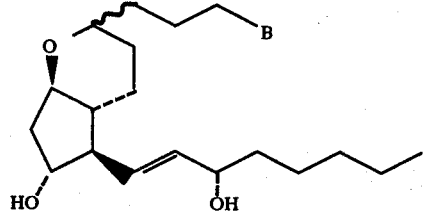

VI-a;

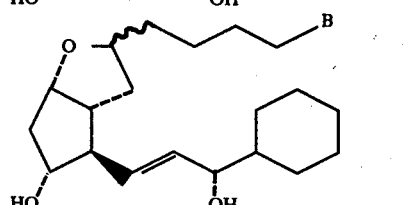

V-b;

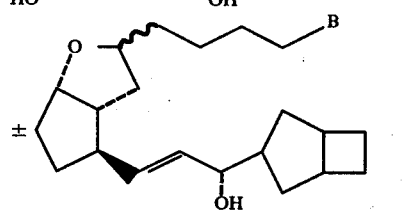

V-c;

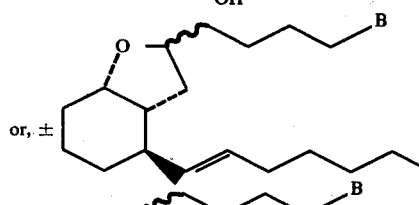

V-d;

or, ±

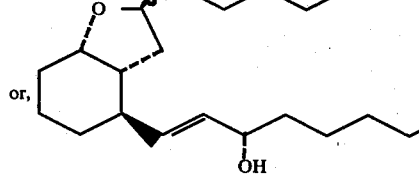

V-e;

or,

Additional 5,6-Dihydro-Prostaglandin I₂ analogues prepared by the process disclosed herein and the first starting materials from which they are prepared are as follows:

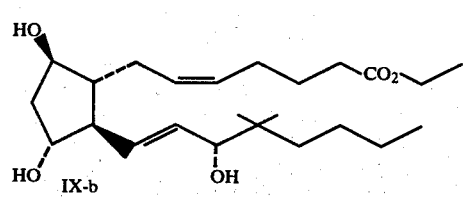

IX-b

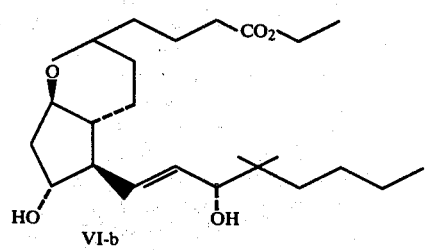

VI-b

-continued

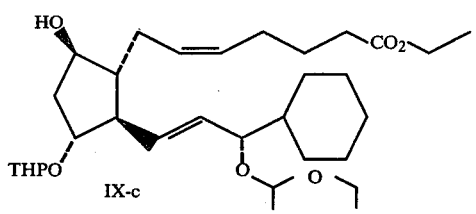
IX-c

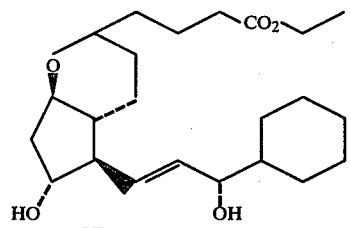
VI-c

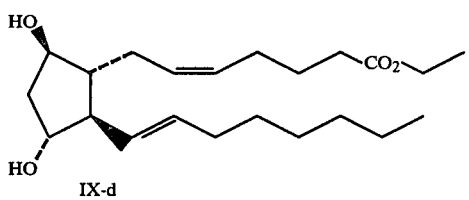
IX-d

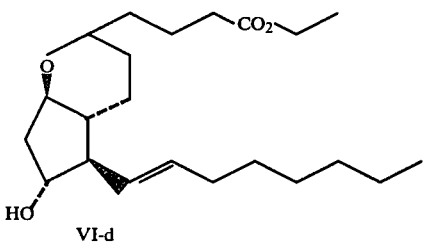
VI-d

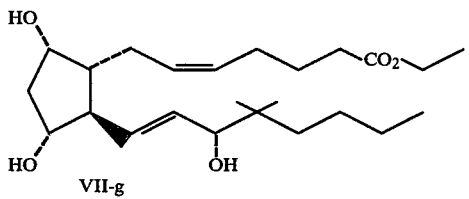
VII-g

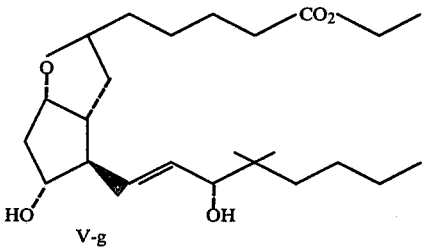
V-g

The scheme for preparation of first starting materials (IX b, c, d, and VII g) is set out in the following Table D, infra, Page 22.

Examples of the mercury salt used in the method include mercuric acetate, mercuric sulfate, mercuric nitrate and the like.

Examples of the polar organic solvent used in the method are methanol, ethanol, propanol, dimethylformamide, dimethylsulfoxide, tetrahydrofuran, acetic acid, trifluoroacetic acid or mixtures thereof. Preferred solvents are dimethylformamide and tetrahydrofuran.

Examples of the borohydride reducing agent used in the method include, but are not limited to, sodium borohydride and potassium borohydride.

The temperature and duration of the reaction depends upon the solvent used and the reactivity of the starting materials used.

Examples of the metallic reducing agent used in the conversion of the acid or esters of V and VI to the corresponding carbinols include, but are not limited to, lithium aluminum hydride and sodium bis (2-methoxyethoxy) aluminum hydride.

Examples of bases which are useful in the conversion of the esters V and VI to the corresponding acids include aqueous alcoholic solutions of potassium or sodium hydroxide and the like.

Non-toxic, pharmacologically acceptable salts of compounds V and VI can be prepared by neutralization of V or VI, where B is $CO_2H$, with an equivalent or an excess amount of the corresponding non-toxic salt-forming organic or inorganic base. The salts are prepared by procedures which are well-known in the art. Suitable salts include sodium, potassium, ammonium and the like. The salts may be isolated by lyophilization of the resulting mixture, or by filtration if sufficiently insoluble, or by similar well-known techniques.

All compounds of this invention can be isolated from reaction mixtures and purified by well-known organic chemistry procedures. For example, the compounds can be isolated by extraction, chromatography, distillation or combination of these procedures. Purification of these compounds can be accomplished by the methods which are well-known in the art for the purification of prostaglandins, lipids, fatty acids, and fatty esters. For example, such methods as reverse phase partition chromatography, counter-current distribution absorption chromatography, preparative paper chromatography, preparative thin layer chromatography, high pressure liquid-liquid chromatography, gas-liquid chromatography and combinations thereof can be used to purify the compounds produced by the process of this invention.

The $PGF_2$ starting materials VII and IX are prepared from corresponding PGE compounds by protection at positions C-11 and C-15 followed by reduction at position C-9 and are well-known as intermediates in the prostaglandin field.

First starting materials VII-a and IX-a are reported by Corey, et al., (*Chem. Commun.*, 658 [1975]) as the methyl ester; (*J. Amer. Chem. Soc.*, 97: 653 [1975]) as the free acid. These compounds are prepared by well-known procedures. For example, $PGF_{2\alpha}$ methyl ester-11,15-bistetrahydropyran-2-yl ether may be prepared by treating $PGF_{2\alpha}$-11,15-bistetrahydropyran-2-yl ether (E. J. Corey et al., *J. Org. Chem.*, 38, 1233 [1973]) with an excess of diazomethane in ether. (M. Fieser and L. F. Fieser, *Reagents for Organic Synthesis*, 1, 191 [1967]). The $PGF_{2\alpha}$ ethyl ester-11,15-bistetrahydropyran-2-yl ether may be prepared by treating $PGF_{2\alpha}$-11,15-bistetrahydropyran-2-yl ether with an excess of diazoethane in ether (M. Fieser and L. F. Fieser, *Reagents for Organic Sysnthesis*, 3, 73 [1972]). The $PGF_{2\alpha}$ propyl ester-11,15-bistetrahydropyran-2-yl ether may be prepared by treating PGF$_{2\alpha}$-11,15-bistetrahydropyran-2-yl ether with an excess of diazopropane (*J. Amer. Oil Chem. Soc.*, 25, 65 [1948]). The corresponding PGF$_{2\beta}$ compounds may be obtained in a similar manner. The bis-protected esters (VII or IX) or the bisprotected cyclized esters (VIII or X) also may be interconverted to a homologous ester by hydrolysis of the ester function with aqueous alcoholic base followed by reaction of the free acid with the desired diazoalkane, such as diazomethane, diazoethane or diazopropane to produce the product where T is an alkyl group having from 1 to 3 carbon atoms.

First starting material VII-b is prepared by reduction of the corresponding bis-substituted PGE$_2$ compound XIV as outlined in Table B. Compound XIV is prepared by reaction of cyclopentenone XIII (C. J. Sih, et al., *J. Amer. Chem. Soc.*, 97, 865 [1975]) with the mixed cuprate XI (Z'=3R-[tetrahydropyran-2-yloxy]; R=cyclohexyl) (H. C. Kluender and G. P. Peruzzotti, *Tetrahedron Letters*, 2063 [1977]).

Corey and D. J. Beames, *J. Amer. Chem. Soc.*, 94, 7210 [1972]).

First starting material VII-d is prepared by reduction of the 9-oxo function of the compound XVIII with L-Selectride ®. Compound XVIII (Z'=H) is prepared by reaction of the mixed cuprate reagent XII (Z'=H; R=n-pentyl) with the cyclohexenane XVII followed by hydrolysis of the ester group. The mixed cuprate reagent XII (Z'=H; R=n-pentyl) is formed in situ by lithiation of iodooctane XI (Z'=H; R=n-pentyl) [C. J. Sih, et al., *J.C.S. Chem. Commun.*, 241 (1972) and references therein] with two equivalents of t-butyllithium at a temperature between −78° C. and −10° C. in ether. The lithio-reagent is then reacted with a cold solution of solubilized copper (I) pentyne in ether (E. J. Corey et al., *J. Amer. Chem. Soc.*, 94, 7210 [1972]). The procedure for preparing the cyclohexanone XVII is described in Example 7 below.

First starting material VII-e is prepared in a similar manner as described above for compound VII-d by

TABLE B

Preparation of First Starting Materials VII b–VII e

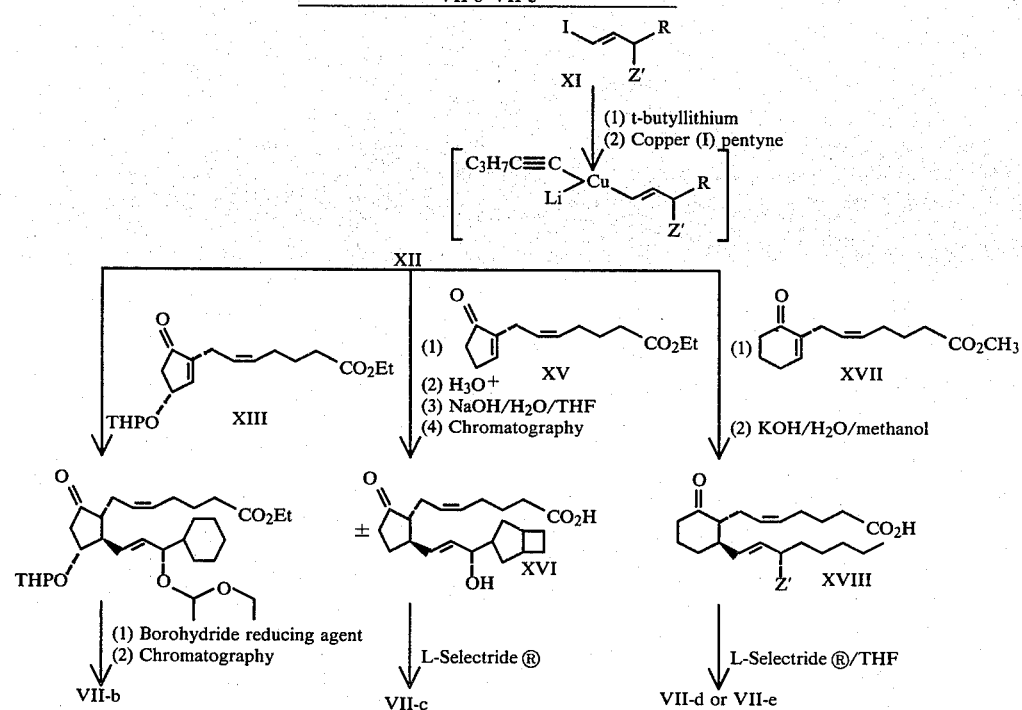

First starting material VII-c is prepared by the reduction of compound XVI with L-Selectride ® (lithium tri-sec-butyl-borohydride in THF, Aldrich Chemical Co.) as outlined in Table B. Compound XVI is prepared by reacting cyclopentenone XV (P. A. Greico and J. J. Reap, *J. Org. Chem.*, 38, 3413 [1973]) with mixed cuprate XII (Z'=1-(ethoxy) ethoxy, R=bicyclo[3.2.0-]hept-3-yl), followed by cleavage of the acid-labile protecting groups, hydrolysis of the ester with base, and chromatography to separte XVI from its 15-epi-ent isomer. Cuprate XII (Z'=1-(ethoxy) ethoxy; R=bicyclo[3.2.0]-hept-3-yl) was formed in situ by reaction of protected iodovinyl alcohol XI-c (see Table C below) with t-butyllithium in ether at −78° C., followed by addition of the resultant lithio-reagent to a solution of solubilized copper (I) pentyne at −78° C. in ether (E. J.

substituting the mixed cuprate XII (Z'=3S-(tetrahydropyran-2-yloxy), R=n-pentyl) (C. J. Sih et al., *J. Amer. Chem. Soc.*, 97, 865 [1975]) for the mixed cuprate XII (Z'=H; R=n-pentyl).

Compound XI-c, used in the preparation of compound VII-c above, is prepared from the corresponding bicycloalkyl acid XXIII via the reaction sequence of Table C by well-known organic chemistry procedures. As outlined in Table C, the bicycloalkyl acid XXIV is converted to the acid chloride XV using an acid chloride forming reagent such as thionyl chloride, oxalyl chloride, phosphorous trichloride and the like as described in Fieser & Fieser, Reagents for Organic Synthesis, I: 1158, J. Wiley & Sons, Inc. (1967). In the conversion of XXV to XXVI, the acid chloride XXV is reacted with acetylene in an inert solvent, such as carbon tetrachloride, methylene chloride or the like, in the presence of a Lewis acid such as aluminum chloride, stannic chloride or the like to produce the β-chlorovinyl ketone XXVI as described in *Chem. Rev.*, 161 (1965) and *Org. Synthe.*, IV: 186, J. Wiley & Sons, Inc. (1963). In the conversion of XXVI to XXVII, the β-chlorovinyl ketone XXVI is converted into the corresponding β-iodo-vinyl ketone XXVII, using a soluble salt, such as sodium iodide, in a polar inert solvent, such as acetone, acetonitrile or the like, as described in *J. Amer. Chem. Soc.*, 94: 7210 (1972). In the conversion of XXVII to XXVIII, compound XXVII is reduced to the corresponding β-iodo or β-bromo-vinyl alcohol using a suitable reducing agent, such as sodium borohydride in alcohol solvent or lithium aluminum hydride in ether solvent as described in *J. Amer. Chem. Soc.*, 94: 7210 (1972). In the conversion of XXVIII to XI-c, compound XXVIII is contacted and reacted with a suitable hydroxyl protecting agent such as dihydropyran or ethylvinyl ether in the presence of an acid catalyst such as p-toluene-sulfonic acid, 98% sulfuric acid or phosphorous oxychloride, or a trialkylsilylchloride such as trimethylsilylchloride, t-butyldimethylsilylchloride, or triphenylmethylbromide in the presence of a basic catalyst such as triethylamine or imidazole. Any hydroxyl protecting group that is removable under mildly acid conditions and is stable to alkyllithium and alkylcopper (I) reagents can also be suitably used, see *J. Org. Chem.*, 37: 1947 (1972).

The bicycloalkyl carboxylic acid (XXIV) is prepared by well-known techniques from commercially available materials. For example, the compound cis-1, 2-cyclobutanedicarboxylic anhydride (XIX) is reduced with a suitable reagent, such as lithium aluminum hydride, lithium borohydride, lithium tri-t-butoxyaluminum hydride or borane, to produce cis-1, 2-bis(hydroxymethyl) cyclobutane. This latter compound is then substituted for trans-1, 2-bis-(hydroxymethyl) cyclobutane in the procedure described in *J. Org. Chem.*, 29 2914 (1964) for the preparation of trans-(bicyclo[3.2.0]hept-3-yl)-carboxylic acid. The product of this procedure is thus cis-bicyclo[3.2.0]hept-3-yl) carboxylic acid (XXIV). This latter compound is used in the reaction sequence further depicted in Table C to produce 1-iodo-3-(1-ethoxy) ethoxy-3-(bicyclo[3.2.0]hept-3-yl)-1E-propane (XI-c).

Referring to Table D, first starting materials IX-d was prepared by reaction of 15-deoxy-PGE$_2$ ethyl ester XXVIII with a borohydride reducing agent in an alcoholic solvent followed by chromatography on Silica Gel or Silicic Acid-Celite (*J. Amer. Chem. Soc.*, 90, 3245 [1968]).

Compound XXVIII was formed by reaction of cyclopentenone XIII with mixed cuprate XII (Z′=H; R=n-pentyl) followed by deprotection of the hydroxyl function by exposure of the intermediate product to aqueous acetic acid (*J. Amer. Chem. Soc.*, 94 7826 [1972]).

First starting material IX-c was isolated along with first starting material VII-b after borohydride reduction of XIV followed by chromatography as set out in Table B, infra, and corresponding textual description.

First starting material IX-b and VII-g were formed from compound XXXIX (16, 16-Dimethyl PGE$_2$ ethyl ester) by borohydride reduction of XXXIX followed by chromatography. Compound XXXIX was formed by reaction of ester XIII with mixed cuprate XII (Z′-OEtOEt, R=1, 1-dimethylpentyl) followed by removal of the hydroxyl protecting groups (*J. Amer. Chem. Soc.*, 97 857, 865[1975]). Mixed cuprate XII (Z′=OEtOEt, R=1, 1-dimethylpentyl) was formed by lithiation of protected iodovinylalcohol XI-d (Table E) with two equivalents of t-butyllithium in ether at between 0° to −78° C. and reaction of the resultant vinyl lithium reagent with solubilized copper (I) pentyne in ether at 0° to −78° C. according to the general method E. J. Corey and D. J. Beames (*J. Amer. Chem. Soc.*, 94, 7210 [1972]). Protected iodovinyl alcohol XI-d was prepared as described in Table E and in the text below.

Referring to Table E, compound XI-d, used in the preparation of compound XXXIX, is prepared from isobutyric acid via the reaction sequence of Table E by well-known organic chemistry procedures. As outlined in Table E, isobutyric acid is converted to 2, 2-dimethylhexanoic acid (XXIX) via sequential reaction of iodobutyric acid with lithium diisopropyl amide (LDA) and n-butyliodide in dry tetrahydrofuran (THF) (*Tetrahedron Lett.*, 1731 [1975]). In the conversion of XXIX to XXX, the acid is reacted with an excess of methyllithium in ether at 0° as described in *Org. Reactions*, 18, 1(1970) to produce the methylketone XXX. The methylketone XXX is reacted sequentially with a base such as sodium hydride or potassium hydride, followed by reaction with methyl or ethyl formate as described by C. Ainworth, *Org. Syn. Coll. Vol.* 4, 536 (1963). Compound XXXI was tosylated by reaction with tosylchloride and triethylamine in ether to form compound XXXII and the tosylate displaced via reaction with an iodide salt such as lithium or sodium iodine to yield iodovinylketone XXXIII as described in (*J. Amer. Chem. Soc.*, 3650[1950]). The conversion of XXXIII to XI-d was accomplished as described for the conversion of compound XXVI to compound XI-c in Table C.

TABLE C

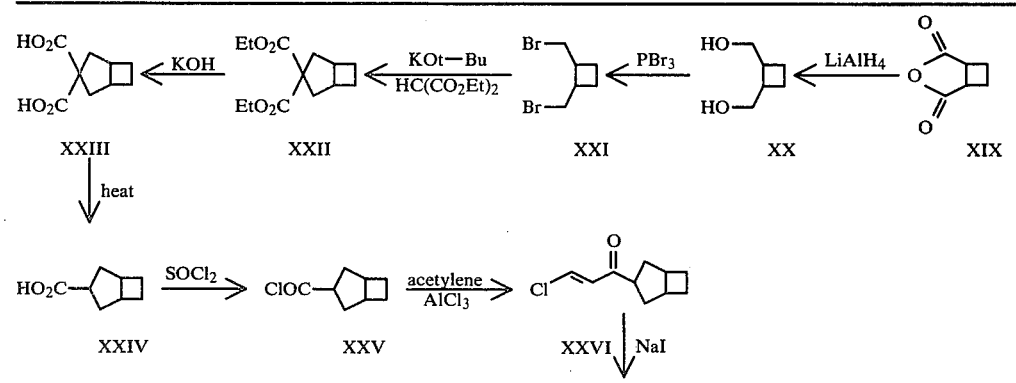

TABLE C-continued

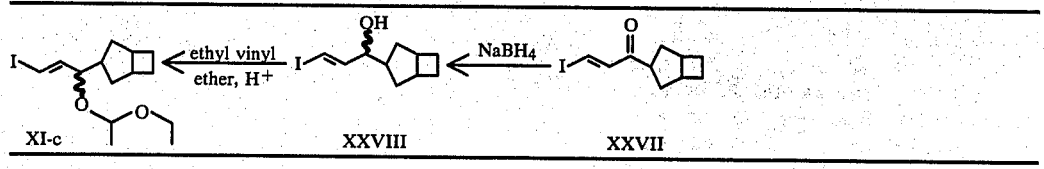

TABLE-D

Preparation of First Starting Materials IXb–IXd, VIIb and VIIg

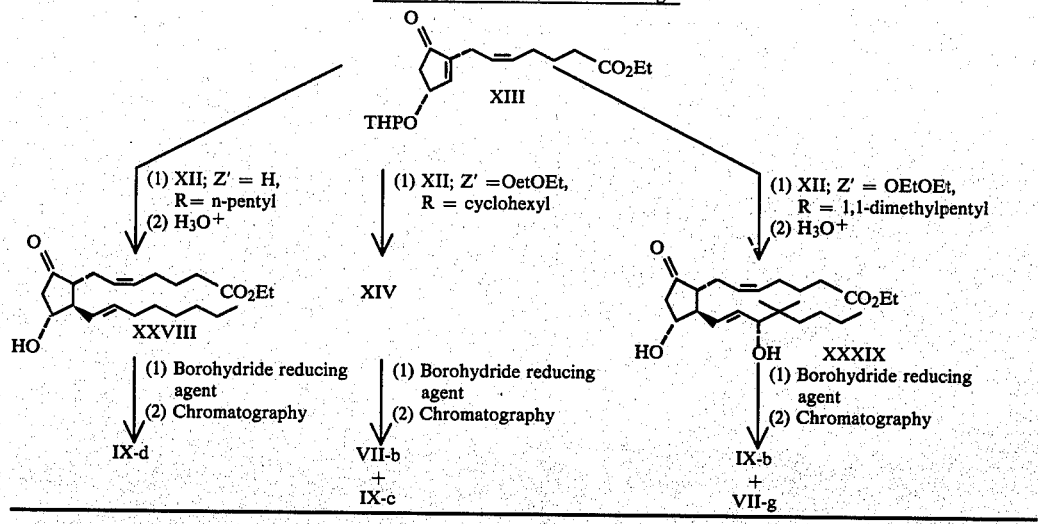

TABLE E

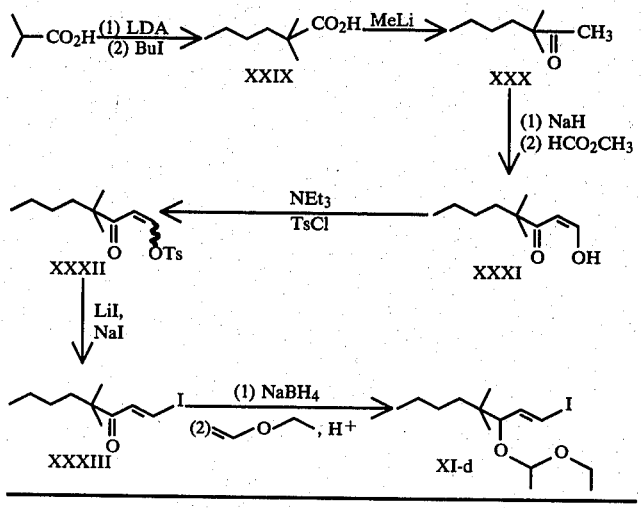

DESCRIPTION OF THE PREFERRED EMBODIMENTS

In the following examples: "THF" is tetrahydrofuran, "ether" is diethyl ether, "Celite" is a trademark for a commercially available diatomaceous earth filter aid. NMR spectra were determined in $CDCl_3$, IR spectra were determined in $CHCl_3$, and mass spectra (ms) are low resolution, 70 eV. Unless otherwise indicated the $R_f$ values were determined using as the elution solvent the organic phase obtained after mixture of ethyl acetate (11 parts), acetic acid (2 parts), isooctane (5 parts) and water (10 parts).

EXAMPLE 1

Preparation of Ethyl 6, 9α-Epoxy-11α, 15S-dihydroxyprost-13E-en-1-oate (V-a, B=$CO_2CH_2CH_3$, TR-4811)

A solution of 131 mg of $PGF_{2\alpha}$ ethyl ester 11, 15-bis-tetrahydropyranyl ether (VII-a) in 6.0 ml of dry methyl formamide was stirred with 740 mg of mercuric acetate for 58 hours at 25° C. The reaction mixture was cooled to 0° C. and treated with 88 mg of sodium borohydride in 13 ml water. The reaction mixture was stirred for 30 minutes at 25° C. then partitioned between brine and ether. The ether layer was dried (MgSO$_4$), filtered and evaporated in vacuo to yield 159 mg of a clear oil. The oil was stirred with 13.0 ml of 65-35-10 (V/V) acetic acid-water-THF for 18 hours, at 25° C. Solvents were removed in vacuo and the residue partitioned between ether and water. The aqueous layer was extracted with ether and the combined ether layers washed with saturated aqueous NaHCO$_3$ and brine, then dried (MgSO$_4$), filtered and evaporated in vacuo to yield 94 mg of a clear oil. Column chromatography (85:15 W/W silicic acid-Celite, benzene-ethyl acetate elution) afforded 16.0 mg of the title compound as an oily yellow solid: R$_f$ 0.37; [α]$_D$+25.7° (c, 0.70, CHCl$_3$), ms m/e 364 (p-H$_2$O), 346, (p-2H$_2$O), 337 (p-OEt), 320 (p-CH$_2$CHOH), 301 (p-2H$_2$O-OEt), 292 (320-Co); nmr δ 0.90 (broad t, 3H), 1.25 (t, J=7.0 Hz, 3H), 4.12 (q, J=7.0 Hz, 2H), 5.50 (m, 2H). No signal corresponding to the 5Z-double bond of starting material VII-a was observed; ir (CHCl$_3$) 2.70, 2.90 (broad), 5.8, 7.25, 10.4μ.

EXAMPLE 2

Preparation of Ethyl 5, 9β-Epoxy-11α, 15S-dihydroxyprost-13E-en-1-oate (VI-a, B=CO$_2$CH$_2$CH$_3$, TR-4829).

A solution of 219 mg of PGF$_{2β}$ ethyl ester 11, 15-bis-tetrahydropyranyl ether, IX-a in 10.0 ml of dimethylformamide was stirred with 1.2 g of mercuric acetate for 47 hours at 25° C. The reaction mixture was cooled to 0° C. and a solution of 147 mg of sodium borohydride in 20 ml of water added dropwise. The reaction mixture was stirred for 0.5 hour at 25° C., then partitioned between brine and ether. The ether layer was dried (MgSO$_4$), filtered and evaporated in vacuo to yield 165 mg of a clear yellow oil. The oil was stirred with 20 ml of 65-35-10 (V/V) acetic acid-water-THF for 18.0 hours at 25° C. The solvents were removed in vacuo and the residue partitioned between ether and water. The aqueous layer was extracted with ether and the combined ether layers were washed with saturated aqueous NaHCO$_3$ and brine, then dried (MgSO$_4$), filtered and evaporated in vacuo to an oil. Column chromatography (85:15 W/W silicic acid-Celite, benzene-ethyl acetate elution) of the oil afforded 15 mg of the title compound as a clear oil: R$_f$ 0.38; [α]$_D$+14.5° C. (μ1.0, CHCl$_3$); ms m/e 364 (p-H$_2$O), 346 (p-2H$_2$O), 320 (p-CH$_2$CHOH), 301 (346-OEt), 292 (320-CO), 249 (320-C$_5$H$_{11}$), 241 (346-[CH$_2$]$_3$CO$_2$C$_2$H$_5$); nmr δ 0.89 (broad t, 3H), 1.25 (t, J=7.0 Hz,3H), 4.15 (q, J=7.0 Hz, 2H), 4.0 (m, 2H), 5.56 (complex, 2H), no signal was observed corresponding to the 5Z-double bond of IX-a; ir 2.78, 2.92 (broad), 5.80, 6.85, 7.25, 10.4μ.

EXAMPLE 3

Preparation of Methyl 6, 9α-Epoxy-11α, 15S-dihydroxyprost-13E-en-1-oate (V-a, B=CO$_2$CH$_3$).

A solution of 86 mg of PGF$_{2α}$ methyl ester-11, 15-bis-tetrahydropyranyl ether in 4.0 ml of dry dimethylformamide was stirred for 48 hours at 25° C. under argon with 95 mg of mercuric acetate, then cooled at 0° C. and treated with 57.5 mg of sodium borohydride in 10.0 ml of water. The reaction mixture was stirred for 30 minutes at 25° C. then partitioned between ether and brine. The ether layer was dried (MgSO$_4$), filtered and evaporated in vacuo to afford 73 mg of a clear oil. The oil was stirred with 6.0 ml of 65-35-10 (V/V) acetic acid-water-THF for 4.0 hours at 40°-50° C. The reaction mixture was evaporated in vacuo and the residue chromatographed (Silica Gel, ethyl acetate) to yield 14.0 mg of the title compound as a clear yellow oil: R$_f$ (EtOAc) 0.135; ir (CHCl$_3$) 2.78, 2.88 (broad), 5.78, 6.95, 10.4μ; mass spectrum m/e 368 (p), 350 (p-H$_2$O), 337 (p-OCH$_3$), 332 (p-2H$_2$O), 319 (p-H$_2$O-OCH$_3$), 306 (p-H$_2$O-CH$_2$CHOH), 278 (306-CO); nmr (CDCl$_3$) δ 0.90 (broad t, 3), 3.66 (s, 3), 3.5–4.6 (complex, 4), 5.5 (m, 2).

EXAMPLE 4

Preparation of 6, 9α-Epoxy-11α-15S-dihydroxyprost-13E-en-1-oic acid (V-a, B=CO$_2$H; TR-4913)

A mixture of 14 mg of methyl 6, 9α-epoxy-11α,15S-dihydroxyprost-13E-en-1-oate, prepared in example 3 above, and 1.0 ml of 5% KOH in 3:1 (V/V) methanol-water was stirred for 2.5 hours at 25° C. The reaction mixture was evaporated in vacuo and the residue dissolved in water. The water layer was extracted with ether. The combined ether extracts were back-washed with water. The combined aqueous layers were acidified and extracted with 1:1 (V/V) ethyl acetate-ether. The extracts were washed with brine, dried (MgSO$_4$), filtered and evaporated in vacuo to yield 17 mg of the title compound as a clear oil: R$_f$ 0.195; ms m/e 336 (p-H$_2$O), 318 (p-2H$_2$O), 292 (p-H$_2$O-CH$_2$CHOH), 265, 264, 247, 235; ir (CHCl$_3$) 2.7–4.2 (broad) 5.75, 7.95, 10.50μ.

EXAMPLE 5

Preparation of Methyl 5, 9β-Epoxy-11α, 15S-dihydroxyprost-13E-en-1-oate (VI-a, B=CO$_2$CH$_3$)

A solution of 62 mg of PGF$_{2β}$ methyl ester-11, 15-bis-tetrahydropyran-2-yl ether in 3.0 ml of dry dimethylformamide was stirred with 68 mg of mercuric acetate for 48 hours at 25° C. under argon. The reaction mixture was cooled to 0° C. and treated with 42 mg of sodium borohydride in 7.0 ml of water. The reaction mixture was stirred for 0.5 hour at 25° C., then partitioned between brine and ether. The ether layer was dried (MgSO$_4$), filtered and evaporated in vacuo to yield 53 mg of a clear oil. The oil was stirred for 48 hours at 25° C. with 5.0 ml of 65-35-10 (V/V) acetic acid-water-THF. The reaction mixture was evaporated in vacuo and the residue chromatographed (Silica Gel, EtOAc) to yield 16.4 mg of the title compound as a white oily solid: R$_f$0.22; nmr δ 0.90 (broad t, 3), 3.66 (s, 3), 3.8–4.4 (complex, 4), 5.50 (m, 2); mass spectrum m/e 368 (p), 350 (p-H$_2$O), 332 (p-2H$_2$O), 319 (p-OCH$_3$), 306 (350-CH$_2$CHOH), 261 (332-C$_5$H$_{11}$), 247 (278-OCH$_3$), 117 [247-(CH$_2$)$_3$CO].

EXAMPLE 6

Preparation of 5, 9β-Epoxy-11α, 15S-dihydroxyprost-13E-en-1-oic acid (VI-a, B=CO$_2$H; TR-4919)

Repeating in a similar manner the procedure of Example 4 above, but replacing methyl 6, 9α-epoxy-11α, 15S-dihydroxyprost-13E-en-1-oate (V-a, B=CO$_2$CH$_3$) with methyl 5, 9β-epoxy-11α, 15S-dihydroxyprost-13-E-en-1-oate (VI-a, B=CO$_2$CH$_3$) prepared in Example 5 above, yields the title compound TR-4919 (VI-a, B=CO$_2$H) as a white solid; mp 84°-87° C.; R$_f$0.15; ms m/e 354 (p), 336 (p-H$_2$O), 318 (p-2H$_2$O), 300.

EXAMPLE 7

This Example illustrates a typical preparation of dl-9a-Homo-6,9α-epoxyprost-13E-en-1-oic acid (V-d, B=CO$_2$H; TR-4914)

A. Preparation of 7-oxabicyclo[4.3.0]non-2-en-8-ol

A solution of 13.8 g of 7-oxabicyclo[4.3.0]non-2-en-8-one, prepared by following the procedures of E. J. Corey and T. Ravindranathan, *Tetrahedron Letters*, 4753 (1971), in 100 ml of dry methylene chloride (passed through Woelm activity grade I alumina prior to use) was stirred at −78° C. under argon as 19.0 ml (107 mmol) of diisobutylaluminum hydride was added dropwise over 0.5 hour. After 3 hours at −78° C. the reaction mixture was quenched at −78° C. by the slow addition of several ml of 10% aqueous hydrochloric acid. The resultant mixture was then stirred in an ice-water bath as 100 ml of 10% hydrochloric acid was added dropwise. The layers which formed were separated and the aqueous phase was extracted twice more with methylene chloride. The combined methylene chloride extracts were washed with brine and then with saturated aqueous sodium bicarbonate. The washed extract was dried (Na$_2$SO$_4$) and evaporated in vacuo to yield 12.3 g of 7-oxabicyclo[4.3.0]non-2-en-8-ol: ir (CHCl$_3$) 14.3, 13.7, 10.87, 9.90, 9.61, 9.27, 6.90, 3.40, and 2.78 to 3.13μ (broad); nmr δ 1.0–3.0 (m, 7H), 4.0–4.8 (m, 2H) and 5.2–6.0 (m, 3H).

B. Preparation of 7-(6-hydroxycyclohex-2-enyl)hept-5Z-enoic acid

A 12.5 g (296 mmol) portion of sodium hydride (57% oil dispersion) was heated with 95 ml of dry dimethylsulfoxide (DMSO) under argon at 65°–75° C. for ca. 2.5 hours until hydrogen evolution had ceased. The mixture was stirred with ice-water cooling as 48.3 g (109 mmol) of 4-carboxybutyltriphenyl-phosphonium bromide (Aldrich) was added as a solid. The resultant deep red mixture was stirred at 0° for several minutes, then at room temperature until most of the salts had dissolved (1 hour). A solution of 12.2 g (87.1 mmol) of 7-oxabicyclo[4.3.0]non-2-en-8-ol in 10 ml of dry DMSO was added dropwise over 2 hours to the vigorously stirred solution. The resultant dark mixture was stirred for 20 hours at room temperature. Water (200 ml) was added and the resultant mixture was extracted three times with ethyl acetate and these extracts were discarded. The remaining aqueous phase was acidified with concentrated hydrochloric acid and then extracted four times with ethyl acetate. The combined extracts were dried (MgSO$_4$) and evaporated in vacuo. The resultant residue was evaporated at 0.1 mm as the pot was warmed to 50° C. and the receiver flask was cooled in an acetone-dry ice bath. The yield of crude orange oil was 32.5 g (theoretical yield 19.5 g) and contained in addition to the desired product, considerable aromatic byproduct as evidenced from an nmr spectrum of this oil. This oil was extracted several times with warm ether-pentane (1:1). The combined extracts were dried (MgSO$_4$) and evaporated in vacuo to give 11.9 g of 7-(6-hydroxycyclohex-2-enyl)hept-5Z-enoic acid. A portion of this product was purified by column chromatography on silicic acid-Celite (85:15) using benzene to ethyl acetate gradient elution to obtain pure 7-(6-hydroxycyclohex-2-enyl)hept-5Z-enoic acid: ir (CHCl$_3$) 9.35, 8.08, 7.10, 6.95, 5.85, 3.40, and 2.78–4.17μ (broad); nmr δ 1.1–2.8 (m, 13H), 2.1 (m, 1H) and 5.2–6.3 (m, 6H); ms m/e 224, 220, 206, 147, 133, 127, 119, 105, 97, 91, 80, 79 (base), 67 and 55.

C. Preparation of 7-(6-oxocyclohex-2-enyl)hept-5Z-enoic acid

A solution of 15.8 g of 7-(6-hydroxyclohex-2-enyl)-hept-5Z-enoic acid (as obtained by ether-pentane extraction as described above) in 300 ml of acetone was stirred with ice-bath cooling as 30 ml of standard Jones reagent was added dropwise. The resultant mixture was stirred for 10 minutes at 0° C. and then quenched by the addition of several ml of isopropyl alcohol. After stirring for another 10 minutes at 0° C. the solvents were removed by evaporation in vacuo. The residue was dissolved in water and extracted several times with ether. The combined ether extracts were washed with brine, dried (MgSO$_4$) and evaporated in vacuo to yield 13.0 g of crude 7-(6-oxocyclohex-2-enyl)hept-5Z-enoic acid as a yellow oil: ir (film) 9.52, 8.07, 7.09, 6.95, 5.85, 3.40, 3.37, and 2.78–4.17 m (broad); nmr δ 1.3–3.2 (m, 13H), 5.2–6.2 (m, 4H) and 8.5 (broad s, 1H).

D. Preparation of Methyl 7-(6-oxocyclohex-1-enyl)hept-5Z-enoic (XVII)

A solution of 13.0 g of crude 7-(6-oxocyclohex-2-enyl)-hept-5Z-enoic acid in 200 ml of dry methanol was stirred under argon as 2 ml of acetyl chloride was added. The resultant yellow solution was left to stand for 2.6 days (on another occasion 16 hours was found to be sufficient). Solvent was removed by evaporation in vacuo and the residue was dissolved in ether and washed with saturated aqueous sodium bicarbonate. The wash solution was back extracted with ether. The combined ether extracts were dried (MgSO$_4$) and evaporated in vacuo to yield 11.6 g of crude methyl 7-(6-oxocyclohex-1-enyl)hept-5Z-enoate as a yellow oil. This product was purified by chromatography on silicic acid-Celite (85:15) using benzene to ethyl acetate gradient elution to give 0.78 g of ca. 80% pure material and 8.41 g of pure material: ir (film) 9.17, 8.55, 8.33, 8.00, 7.30, 7.04, 5.95, 5.74, and 3.39μ; nmr δ 1.3–2.5 (m, 12H), 2.9 (m, 2H), 3.67 (s, 3H), 5.45 (m,2H) and 6.7 (m,1H).

E. Preparation of dl-9a-Homo-9-oxoprosta-5Z, 13E-dien-1-oic acid (XVIII, Z'=H)

A solution of 1.24 g of 1-iodo-oct-1E-ene (C. J. Sih, et al., *J.C.S. Chem. Commun.*, 241 [1972]) in 24.0 ml of ether was cooled to −78° C. with stirring under argon and 5.81 ml of 1.78 N t-butyllithium in pentane injected. After 2.0 hours at −78° C., the reaction mixture was transferred into a stirred −78° C. solution of 610 mg of copper (I) pentyne in 14.0 ml ether (solubilized at 25° C. with 1.70 ml of hexamethylphosphorous triamide [HMPTA]). The resultant complex was stirred for 30 minutes at −78° C.; then a solution of 1.05 g of compound XVII prepared in Example 7 D above in 5.0 ml ether was added dropwise. The reaction mixture was stirred for 15 minutes at −78° C., 1.5 hours at −10° C., 0.5 hour at 0° C. and 0.5 hour at 25° C. The reaction was quenched by addition of 20% aqueous ammonium sulfate, the layers separated, the aqueous layer extracted twice with ether. The combined extracts were washed with 2% aqueous sulfuric acid, saturated aqueous sodium bicarbonte and brine, then dried (MgSO$_4$), filtered and evaporated in vacuo to yield 1.41 g of a yellow oil. The oil was stirred with 30 ml of 3% potassium hydroxide in 3:1 (V/V) methanol-water for 5.0 hours at 25° C. The reaction mixture was evaporated in vacuo then further processed as described in Example 4 to yield 1.15 g crude XVIII (Z'=H) as a yellow oil. The crude product was further purified by column chromatography (85:15 W/W silicic acid-Celite, benzene-ethyl acetate elution) to afford 877 mg of the title compound XVIII (Z'=H) as a light yellow oil, $R_f$ 0.70; nmr δ 0.90 (broad t, 3H), 2.7–1.0(complex, 29H), 5.40 (m, 4H), 8.86 (broad, 4H).

F. Preparation of dl-9a-Homo-9a-hydroxyprosta-5Z, 13E dien-1-oic acid (VII-d, B=CO$_2$H)

A solution containing 0.3 mmol of compound XVIII, prepared in Example 7 E above, in 1.0 ml of THF was stirred with 1.0 ml of 1 M L-Selectride ® at −78° C. for 1.0 hour under argon. The reaction was quenched by the addition of 3.0 ml of 65-35-10 (V/V) acetic acid-water-THF. The reaction mixture was warmed to 25° C. and was stirred for 2.0 hours. The reaction mixture was evaporated in vacuo and the residue dissolved in ether. The solution was washed with 10% hydrochloric acid and brine, then dried (MgSO$_4$), filtered and evaporated to yield the title compound VII-d as a yellow oil: $R_f$(ethyl acetate) 0.45.

G. Preparation of dl-9a-Homo-6, 9α-epoxyprost-13E-en-1-oic acid (V-d, B=CO$_2$H, TR-4914)

Repeating in a similar manner the procedure of Example 1 above, but substituting compound VII-d prepared in Example 7 F above for compound VII-a and omitting the aqueous acid treatment of Example 1 yields the title compound TR-4914 as a clear oil: $R_f$(2:1 hexane-ethyl acetate) 0.14; nmr δ 0.90 (broad t, 3), 2.40 (broad t, 2), 4.04 (complex, 2), 5.35 (m, 2), 8.35 (broad, 1): ir (CHCl$_3$) 2.8–4.2 (broad), 5.85, 6.85, 10.50µ.

EXAMPLE 8

This Example illustrates a typical preparation of 9-Deoxy-9a-Homo-6, 9α-epoxy-15S-hydroxyprost-13E-en-1-oic acid (V-e, B=CO$_2$H, TR-4921).

A. Preparation of 9a-Homo-9-oxo-15S-(tetrahydropyran-2-yloxy) prosta-5Z, 13E-dien-1-oic acid (XVIII, Z=15S-tetrahydropyran-2-yloxy)

Repeating in a similar manner the procedure of Example 7 E above, but replacing 1-iodo-oct-1E-ene with 1-iodo-3S-(tetrahydropyran-2-yloxy) oct-1E-ene (C. J. Sih et al., *J. Amer. Chem. Soc.*, 97, 865 [1975]) yields the title compound (XVIII, where Z is 15S-(tetrahydropyran-2-yloxy) as a yellow oil: $R_f$(9:1 CHCl$_3$-hexane) 0.48; nmr δ 0.90 (broad t, 3H), 3.3–4.2 (complex, 3H), 4.8 (m, 1H), 5.4 (m, 4H), 7.9 (broad, 2H); ir (CHCl$_3$) 2.8–4.0 (broad), 5.90, 10.40µ.

B. Preparation of 9a-Homo-9α-hydroxy-15S-(tetrahydropyran-2-yloxy) prosta-5Z, 13E-dien-1-oic acid (VII-e)

A solution of 135 mg (0.3 mmol) of compound XVIII (Z=15S tetrahydropyran-2-yloxy) prepared in Example 8 A in 1.0 ml of THF was stirred with 1.0 ml of 1 M L-Selectride ® at −78° C. for 1.0 hour under argon. The reaction was quenched by the dropwise addition of 3.0 ml of 65-35-10 (V/V) acetic acid-water-THF. The cooling bath was removed and the reaction mixture stirred at 25° C. for 2.0 hours. The reaction mixture was evaporated in vacuo and the residue dissolved in ether. The solution was washed with 10% hydrochloric acid and brine, then dried (MgSO$_4$), filtered and evaporated to yield 130 mg of compound VII-e as a light brown oil: $R_f$(ethyl acetate) 0.39; nmr δ 0.92 (broad t, 3), 3.3–4.3 (complex, 4), 4.8 (m, 1), 5.42 (m, 4), 6.85 (broad, 2); ir (CHCl$_3$) 2.8–4.0 (broad), 5.90, 6.88, 9.80, 10.40µ.

C. Preparation of 9-Deoxy-9a-Homo-6, 9α-epoxy-15S-hydroxyprost-13E-en-1-oic acid (V-e, B=CO$_2$H, TR-4912)

Repeating in a similar manner the procedure of Example 1 above, but substituting VII-e, prepared in Example 8 B, for VII-a yields compound TR-4921 as a clear oil: $R_f$ (ether) 0.24; $[\alpha]_D$+2.4° (c 0.63, CHCl$_3$); nmr δ 0.90 (broad t, 3), 2.35 (broad, t, 2), 4.03 (complex, 3), 3.42 (complex, 4); ir (CHCl$_3$) 2.8–4.4 (broad), 5.85, 6.85, 9.40, 10.50µ.

EXAMPLE 9

This example illustrates a typical preparation of dl-6, 9α-Epoxy-15R-hydroxy-16, 19-methano-18, 20-methanoprost-13E-en-1-oic acid (V-c, B=CO$_2$H, TR-4938)

A. Preparation of cis-1, 2-bis-(hydroxymethyl) cyclobutane (XX)

A solution of 5.0 g (0.40 mmol) of cis-1, 2-cyclobutane dicarboxylic anhydride (Aldrich # 14, 543-2) in 50 ml of ether and 75 ml of THF was added in small portions to a 0° C. slurry of 21.0 g of lithium aluminum hydride in 200 ml of ether in a 500 ml three-necked round-bottomed flask equipped with a reflux condenser, mechanical stirring, addition funnel and argon inlet. The reaction mixture was warmed to 50° C. and stirred for 1 hour. Ethyl acetate (31.0 ml) was added dropwise, followed by 21.0 ml water, 21.0 ml 15% aqueous sodium hydroxide and 40 ml of water. The reaction mixture was stirred for 18 hours at 25° C., then filtered. The filtrate was washed with brine and vacuum distilled to afford 21.5 g of cis-1, 2-bis-(hydroxymethyl)-cyclobutane as a clear oil: bp 94°–97° (vacuum pump); ir (CHCl$_3$) 2.78, 3.0 (broad), 5.9µ; nmr δ 1.10–2.30 (m, 4), 2.65 (m, 2), 3.6 (m, 4) and 4.65 (broad t, 2).

B. Preparation of cis-1, 2-bis-(bromomethyl) cyclobutane (XXI)

To 44 g of phosphorous tribromide (−10° C.) was added dropwise 10.7 g of distilled XX over a 1 hour period. The reaction mixture was warmed to 25° C. and stirred for 2 hours, then heated to 80°–85° C. for 18 hours. The reaction mixture was cooled in ice and cold water added. The layers were separated and the aqueous layer was extracted with methylene chloride. The organic extracts were combined, washed with 5% aqueous sodium carbonate and water, then distilled to yield 13.8 g of the title compound XXI as a purple oil, bp 86° (vacuum pump): ir (CHCl$_3$) 3.4, 7.0–8.1µ (no OH signal observed); nmr δ 1.3–2.5 (m, 4), 2.8 (m, 2), and 3.5 (m, 2).

C. Preparation of 3, 3-bis-(ethoxycarbonyl) bicyclo-[3.2.0]heptane (XXII)

In a 250 ml round-bottomed flask equipped with mechanical stirring, reflux condenser, addition funnel and argon inlet was placed 20.2 g of XXI, 12.4 ml diethylmalonate, and 72 ml of dry t-butanol. The reaction mixture was refluxed and a solution of 19.9 g of potassium-t-butoxide in 123 ml of t-butanol was added over 6 hours. The reaction mixture was refluxed for 15 hours.

The resulting reaction mixture was cooled by external application of an ice-water bath and an equal volume of water added. The mixture was extracted with ether. The ether extracts were washed with 3 N hydrochloric acid and 5% aqueous sodium bicarbonate, then dried (MgSO$_4$), filtered and distilled in vacuo to yield 10.3 g of the compound XXII as a clear oil: bp 100°–105° C. (vacuum pump); ir (CHCl$_3$) 5.85μ; nmr δ 1.22 (pair of t, J=7.0Hz, broad), 4.37 (quartet, 4).

D. Preparation of bicyclo[3.2.0.]heptane-3, 3-dicarboxylic acid (XXIII)

A solution of 10.3 g of XXI in 68 ml of 16% potassium hydroxide in 1:1 methanol-water was refluxed for 16 hours under argon. The solvents were removed in vacuo and the residue dissolved in a minimum amount of water. The solution was acidified with concentrated hydrochloric acid and the precipitated acid isolated by vacuum filtration to yield 6.9 g of the title compound XXIII as a white solid, mp 161°–170°; nmr (DMSO-d$_6$); δ 7.65 (broad s, 2).

E. Preparation of cis-(bicyclo[3.2.0]hept-3-yl) carboxylic acid (XXIV)

Compound XXIII (6.90 g) was heated at 190° C. under argon for 1 hour to afford 4.75 g of the title compound XXIV as a brown oily solid: nmr (CDCl$_3$) δ 10.18 (broad s, 1): ir (CHCl$_3$) 2.75–4.4 (broad), 5.85, 6.40μ.

F. Preparation of cis-(bicyclo[3.2.0]hept-3-yl) carboxylic acid chloride (XXV)

A mixture of 4.60 ml of thionyl chloride and 4.75 g of XXIV was stirred for 14.5 hours at 25° C. then distilled to afford 4.10 g of XXV as a clear oil; bp 80°–85° C.; ir (CHCl$_3$) 3.46, 5.60, 6.95, 9.70μ.

G. Preparation of 1-chloro-3-(bicyclo[3.2.0]hept-3-yl-1E-propen-3-one (XXVI)

A 50 ml three-necked, round-bottom flask was equipped with an acetylene inlet, reflux condenser, gas outlet bubbler, and mechanical stirring. Acetylene was passed through the flask for 5 minutes, then the flask was charged with 20 ml of carbon tetrachloride, ice bath cooling applied and acetylene passed through the solvent for 10 minutes more. Aluminum chloride (3.73 g) was introduced. Acetylene was bubbled through the stirred slurry for 5 minutes, then 3.82 g (23.8 mmol) of XXV was added dropwise over 20 minutes with the acetylene flow stopped. Acetylene was passed through the stirred reaction mixture for 4.0 hours at 0° C. The reaction mixture was poured onto a mixture of 100 g of ice and 25 ml of brine. The organic phase was removed and the aqueous phase extracted three times with ether. The extracts were washed with 10% aqueous hydrochloric acid and saturated aqueous sodium bicarbonate, then dried (MgSO$_4$), filtered, and distilled to yield 1.95 g of XXVI as an orange oil: bp 95°–97° C. (high vacuum); nmr δ 6.66 (d, J=14.0Hz, 1), 7.36 (d, J=14.0Hz, 1)

H. Preparation of 1-iodo-3-(bicyclo[3.2.0]hept-3-yl)-1E-propen-3-one (XXVII)

A solution of 4.52 g of XXVI in 24.0 ml of dry acetone was refluxed for 16.0 hours under argon. The reaction mixture was cooled and evaporated in vacuo. Water was added and the residue with ether. The extracts were washed with aqueous sodium thiosulfate and brine, dried (MgSO$_4$), filtered and evaporated in vacuo to yield 6.32 g of XXV as an orange oil: nmr δ 7.27 (d, J=15.0Hz, 1) 7.99 (d, J=15.0 Hz, 1).

I. Preparation of 1-iodo-3-(bicyclo[3.2.0]hept-3-yl)-1E-propen-3RS-ol (XXVIII)

A solution of 6.30 g of XXVII, in 80 ml of methanol was cooled to −10° C. and 3.45 g of sodium borohydride added in small portions over 5 minutes. The reaction mixture was stirred for 1.0 hour at −10° C. The methanol was evaporated in vacuo and the residue was partitioned between ether and brine. The ether layer was dried (MgSO$_4$), filtered and evaporated in vacuo to afford 6.38 g of XXVIII as a yellow oil: nmr δ 4.2 (m, 1), 6.26 (d, J=15.0Hz, 1), 6.62 (dd, J=15.0 and 6.0 Hz, 1).

J. Preparation of 1-iodo-3RS-(1-ethoxyethoxy)-3-(bicyclo[3.2.0]hept-3-yl)-1E-propene (XI-c)

A solution of 6.30 g XXVIII in 10.0 ml of neat ethyl vinyl ether was stirred at 25° C. under argon and two drops of phosphorous oxychloride added. The reaction mixture was stirred for 18.0 hours at 25° C. then diluted with ether and poured into saturated aqueous sodium bicarbonate. The layers were separated. The ether layer was washed with brine, dried (MgSO$_4$), filtered and distilled (bulb to bulb, vacuum pump) to yield 940 mg of XI-c as a yellow oil: nmr δ 3.5–4.2 (m, 3), 4.8 (m, 1), 6.0–7.0 (m, 2).

K. Preparation of dl-15R-Hydroxy-9-oxo-16, 19-methano-18,-20-methanoprosta-5Z, 13E-dien-1-oic acid (TR-4101, XVI) and dl-15S-hydroxy-9-oxo-16, 19-methano-18, 20-methanoprosta-5Z, 13E-dien-1-oic acid (TR-4102, 15-epi-XVI)

A solution of 940 mg XI-c (3.71 mmol) in 18.0 ml ether was cooled to −78° C. with stirring under argon and 3.38 ml of 1.7 N t-butyllithium in hexane injected. The reaction mixture was stirred for 2.0 hours at −78° C. then transferred into a stirred −78° C. solution of 328 mg of copper (I) pentyne in 10.0 ml ether (solubilized at 25° C. by the addition of 0.92 ml of HMPTA). The resultant complex was stirred for 30 minutes at −78° C., then a solution of 526 mg (2.37 mmol) of XV (P. A. Greico et al., *J. Org. Chem.*, 38: 3413 [1973]) in 6.0 ml of dry ether was added dropwise. The reaction mixture was stirred 15 minutes at −78° C. then warmed to 0° C. over 1.5 hours via application of an ice-salt bath. The reaction mixture was stirred for 0.5 hour at 0° C. and for 0.5 hour at 25° C., then processed as described in Example 7 E above to yield 1.07 g of a light yellow oil.

The oil was stirred with 18.5 ml of 5% KOH in 3:1 methanol-water for 2.0 hours at 25° C. then processed as described in Example 4, above, and the crude product further purified by column chromatography (85:15 silicic-acid-Celite, benzene-ethyl acetate elution) to yield 143 mg of 15-epi-XVI as a yellow oil: R$_f$ 0.64; nmr δ 0.6–2.8 (m, 39), 4.15 (m, 1), 5.5 (m, 4), 6.4 (s, 2); ir (CHCl$_3$) 2.78, 2.7–4.2, 5.79, 5.85, 10.30μ; and 171 mg of XVI as a yellow oil: R$_f$ 0.60; spectral properties similar to 15-epi-XVI, above.

L. Preparation of dl-9α, 15R-Bis-Hydroxy-16, 19-methano-18, 20-methanoprosta-5Z, 13E-dien-1-oic acid (VII-c)

Repeating in a similar manner the procedure of Example 8 B above, but substituting XVI for XVIII yields VII-c as a clear oil: $R_f$ 0.52.

M. Preparation of dl-6, 9α-Epoxy-15R-hydroxy-16, 19-methano-18, 20-methanoprost-13E-en-1-oic acid (V-c, B=CO$_2$H, TR-4937)

Repeating in a similar manner the procedure of Example 1 above but omitting the aqueous acid hydrolysis step and substituting VII-c for VII-a yields the title compound (TR-4937) as a clear oil: $R_f$ 0.53; nmr δ 3.3–4.7 (complex, 3), 5.6 (m, 2), 5.7 (broad s, 2); ir (CHCl$_3$) 2.78, 2.8–4.2, 5.85, 6.95, 7.85, 10.40μ; ms m/e 362 (p), 344 (p-H$_2$O), 326 (p-2H$_2$O), 316 (344-CO), 367 (p-C$_5$H$_{11}$) and 261 (p-(CH$_2$)$_4$ COOH).

EXAMPLE 10

This example illustrates a typical preparation of Ethyl 6, 9α-Epoxy-11α, 15R-dihdroxy-16, 20-methanoprost-13E-en-1-oate (V-b, B=CO$_2$Et; TR-4965).

A. Preparation of Ethyl 9α-Hydroxy-11α-(tetrahydropyran 2-yloxy)-15R-(1-ethoxyethoxy)-16, 20-methanoprosta-5Z, 13E-dien-1-oate (VII-b)

Repeating the procedure of Example 7 E above, replacing 1-iodo-oct-1E-ene with 1-iodo-3R-(1-ethoxyethoxy)-3-cyclohexyl-prop-1E-ene (H. C. Kluender et al., Tetrahedron Letters, 2063 [1977]) and replacing XVIII with XIII (C. J. Sih, Sih, et al., J. Amer. Chem. Soc., 97, 865 [1975]) affords ester XIV. (The basic ester hydrolysis step was omitted). Repeating the procedure of Example 8 B above, but replacing XVIII with XIV above yields compound VII-b as a clear oil: $R_f$ (ether) 0.51; nmr δ 1.22 (complex, 9), 3.2–4.3 (complex, 5), 4.12 (q, J=7.0 Hz, 2), 4.7 (ciomplex, 2) and 5.4 (m, 4).

B. Preparation of Ethyl 6, 9α-Epoxy-11α, 15R-dihyroxy-16, 20-methanoprost-13E-en-1-oate (V-b, B=CO$_2$CH$_2$CH$_3$; TR-4965)

A solution of 160 ml (0.28 mmol) of VII-b in 7.0 ml THF was stirred with 35 mg of anhydrous calcium carbonate and 150 mg of mercuric trifluoroacetate (Aldrich Chemical Co.) for 1.0 hour at 25° C. The reaction mixture was cooled to −20° C. and treated dropwise with a solution of 115 mg of sodium borohydride in 15 ml of absolute ethanol. The reaction mixture was stirred for 1.0 hour at −20° C., then partitioned between brine and ether. The ether layer was dried (MgSO$_4$), filtered and evaporated in vacuo to yield an oil. The oil was stirred with 15.0 ml of 65-35-10 (V/V) acetic acid-water-THF for 4.0 hours at 40°–50° C. The reaction mixture was evaporated in vacuo, and the product isolated by column chromatography (Silica gel, ethyl acetate) to yield 12 mg of compound VII-b (B=CO$_2$CH$_2$CH$_3$) as a clear oil, $R_f$ (benzene-dioxane) 0.21; $[α]_D$+14.4° (c 1.26, CHCl$_3$); nmr 1.22 (t, J=7.0 Hz, 3), 2.35 (broad t, 2), 3.4–4.6 (complex, 6) 4.15 (q, J=7.0 Hz, 2), 5.5 (m, 2); ir (CHCl$_3$) 2.78, 2.95, 5.80, 6.90, 7.30, 10.40ρ; ms m/e 376 (p-H$_2$O), 358 (p-2H$_2$O) 349 (p-OCH$_2$CH$_3$), 332 (p-H$_2$O-CH$_2$CHOH), 313, 304.

EXAMPLE 11

This example illustrates a typical preparation of 6, 9α-epoxy-16, 20-methanoprost-13E-ene-1, 11α,15R-triol (V-b,V=CH$_2$OH; TR-4970)

A solution of 43 mg (0.11 mmol) of V-b, B=CO$_2$Et, prepared in Example 10 B, in 1.0 ml of dry THF was added dropwise to a stirred, −10° C. solution of 0.4 ml of Red-al (sodium bis-[2-methoxyethoxy]-aluminum hydride, 70% in benzene or toluene, Aldrich Chemical Co.) in 1.0 ml of dry THF under argon. The reaction mixture was stirred for 1.0 hour at 0° C. and for 0.5 hour at 25° C. The reaction mixture was partitioned between 10% aqueous hydrochloric acid and ether. The ether layer was washed with brine, then dried (MgSO$_4$), filtered and evaporated in vacuo. The crude product was purified (preparative TLC on Silica Gel, ethyl acetate) to yield the pure title compound V-b, B=CH$_2$OH (11 mg) as a clear oil: $R_f$(ethyl acetate) 0.09; $[α]_D$+27.3° (c 1.1, CHCl$_3$); nmr δ 3.65 (broad, t, 2), 3.3–4.5 (complex, 7) 5.5 (m, 2); ir (CHCl$_3$) 2.78, 2.95, 6.90, 10.40μ.

EXAMPLE 12

A. Preparation of Ethyl 9β-Hydroxy-11α-(tetrahydropyran-2-yloxy)-15R-(1-ethoxyethoxy)-16,20-methanoprosta-5Z,13E-dien-1-oate (IX-c)

A solution of 2.62 g ester XIV, prepared as described in Example 10 a, in 32.0 ml of absolute ethanol was cooled to 0° C. whereupon 380 mg of sodium borohydride was added in small portions. After 1 hour at 0° C., solvent was removed by evaporation in vacuo and the residue partitioned between ether and water whereupon the aqueous layer was extracted with ether. The ether extracts were washed with brine, then dried (MgSO$_4$), filtered and evaporated in vacuo to yield 2.59 g of a mixture of VII-b and IX-c as a brown oil. The components were separated by column chromatography (Silica Gel, 2:1 hexane-ethyl acetate to ethyl acetate gradient elution) to afford 2.54 mg IX-c as a clear oil, $R_f$ (ether) 0.51 and 682 mg of VII-b as a yellow oil, $R_f$ (ether) 0.61.

B. Preparation of Ethyl 5, 9β-Epoxy-11α,15-dihydroxy-16,20-methanoprost-13E-en-1-oate (VI-c, TR-4973)

Repeating the procedure of Example 10 B above, except for replacing VII-b with IX-c and extending the initial reaction time to 18 hours at 25° C. afforded VI-c, as a clear oil, $R_f$(ethyl acetate) 0.21; $[α]_D$+28.3° (c 0.93, CHCl$_3$); ms m/e 376 (p-H$_2$O) 358 (p-2H$_2$O) nmr 1.27 (t, J=7.0 Hz, 3), 2.75 (broad s, 2), 3.3–4.3 (complex, 4) 4.15 (q, J=7.0 Hz, 2), 5.55 (complex, 2); ir (CHCl$_3$) 2.70, 2.90 (broad), 5.85, 6.90, 7.25, 10.40μ.

EXAMPLE 13

A. Preparation of Ethyl 9β,11α-Dihydroxyprosta-5Z,13E-dien-1-oate (IX-d) and Ethyl 9β,11α-Dihydroxyprosta-5Z,13E-dien-1-oate (VII-f)

Repeating the procedure of Example 7 E above, except for replacing XVII with XIII, affords protected ester XXVII. (The basic ester hydrolysis step was omitted). The protected groups were hydrolyzed by stirring the crude product with 65-35-10 HOAC-THF-H$_2$O for 18 hours at 30° C. The reaction mixture was evaporated in vacuo to yield crude XXVIII.

Repeating the procedure of Example 13 A above, replacing IX with XXVIII affords IX-d as a yellow oil, $R_f$ (1:1 ethyl acetate-hexane) 0.145; nmr 0.90 (broad t, 3), 1.26 (t, 3), 4.15 (q, 2), 3.7–4.3 (complex, 2), 5.48 (complex, 4); ir (CHCl$_3$) 2.70, 2.85 (broad); 5.80, 7.25, 10.40$\mu$; ms m/e 366 (p), 348 (p-H$_2$O), 330, 304; and VII-f as a yellow oil; $R_f$(1:1 ethyl acetate-hexane) 0.22; nmr 0.90 (t, 3), 1.28 (t, 3), 4.16 (q, 2), 3.5–4.5 (complex, 2), 5.42 (complex, 4); ir (CHCl$_3$) 2.86 (broad) ;b 5.82, 7.25, 10.40$\mu$; ms m/e 366, 348, 330, 304.

B. Preparation of Ethyl 5, 9$\beta$-Epoxy-11=-hydroxyprost-13E-en-1-oate (VI-d, TR-7018)

Repeating the procedure of 10 B (above) but replacing VII-b and IX-d, extending the initial reaction time to 18 hours and omitting the aqueous acid hydrolysis step afforded VI-d after chromatography (Silica Gel, 3:1 hexane ethyl acetate) as a clear oil, $R_f$ (1:1 ethyl acetate-hexane) 0.38; $[\alpha]_D$+24.7° (c 1.05, CHCl$_3$); nmr 0.90 (broad t, 3), 1.25 (t, 3), 4.2 (q, 2), 3.3–4.3 (complex, 3), 5.46 (complex, 2); ir (CHCl$_3$) 2.78, 2.90 (broad), 5.85, 7.25, 9.10, 10.40$\mu$; ms m/e 348 (p-H$_2$O), 337, 323, 322, 305, 304.

EXAMPLE 14

A. 2,2-Dimethylhexanoic Acid (XXIX)

A solution of 102 g (1.02 mol) of diisopropylamine (distilled from calcium hydride) in 730 ml of dry THF was stirred under argon in an ice-bath as a full bottle (1.0 mol) of solution of n-butyllithium in hexane (Alpha, 2.4 M, ca. 417 ml) was added dropwise at a rate such that the temperature held below 8°. About halfway through the addition, the ice-bath was replaced by an ice-methanol bath to better control the temperature at 0° C. throughout the rest of the addition. The resultant mixture was kept in the cold bath and stirred for 15 minutes before a 41.6 g (0.427 mol) portion of isobutyric acid was added dropwise, again keeping the temperature below 0°. Final portions of the acid were rinsed into the reaction mixture with several ml of dry THF. After another 15 minutes a 57 ml (0.499 mol) portion of 1-iodo-butane was added dropwise. After the addition was completed, the ice-bath was removed and the resultant mixture was stirred for 2 hours. The ice-bath was used again as the resultant mixture was quenched by the dropwise addition of a solution of 200 ml of concentrated hydrochloric acid in 640 ml of water. The phases were separated and the aqueous phase was back-extracted with ether. The combined extract was washed with aqueous sodium bisulfite, dried (MgSO$_4$) and evaporated in vacuo. The residue was distilled at 20 mm to yield 56.8 g of XXIX as an oil, bp 110°–113°; nmr 0.90 (3, broad t, J=5.7 Hz), 1.18 (6, s) and 1.0–2.0 (6, m).

B. 3,3-Dimethyl-2-heptanone (XXX)

A solution of 14.4 g (100 mmol) of 2,2-dimethylhexanoic acid (XXIX) in 100 ml of dry ether was stirred a 0° C. under argon as 130 ml (237 mol) of a solution of methyllithium (1.82 M) in ether was added dropwise. The resultant mixture was stirred with ice-bath cooling for 1 hour and then without cooling overnight. It was then poured into a vigorously stirred 500 ml portion of water in a large beaker. The phases were separated and the aqueous phase was back-extracted twice with ether. The combined extract was dried (MgSO$_4$) and evaporated in vacuo. The residue was distilled at 20 mm to yield 12.7 g of XXX as a colorless oil, bp 125°–130°; $R_f$ (CHCl$_3$) 0.54; nmr 0.9 (3, broad t, J=6.0 Hz), 1.12 (6, s), 1.0–1.8 (6, m) and 2.14 (3, s); ir (film) 8.85, 7.45, 6.80, 5.85, 3.50, 3.41 and 3.38$\mu$.

C. 4,4-Dimethyl-1-hydroxyoct-1-en-3-one (XXXI)

Sodium hydride (9.9 g of 56% oil dispersion) was rinsed twice with dry hexane and then dried by evaporation in vacuo. Argon was used to release the vacuum whereupon ether (140 ml) followed by 40 ml of methylformate was added to the flask containing the sodium hydride. The resultant mixture was stirred under argon as a solution of 22.3 g (157 mmol) of XXX in 35 ml ether was added dropwise. After CA 1/4 of the solution had been added it was noted that no significant gas evolution was taking place. A 3 ml portion of methanol was added dropwise before the remainder of XXX was added. Shortly after the addition was complete another portion (50 ml) of dry ether was added to the reaction mixture to facilitate stirring. After 3.5 hours the reaction mixture was quenched by the addition of water. The phases were mixed thoroughly and then separated, whereupon the ether phase was extracted twice more with water and then three times with 1 N aqueous sodium hydroxide. The water and basic extract were each made acidic with the addition of concentrated hydrochloric acid and then extracted several times with ether. The ether extracts were dried (MgSO$_4$) and evaporated in vacuo. The yield from the acidified water phases was 5.0 g and from the acidified basic extracts was 13.8 g of XXXI. This product was not further purified for the next reaction; $R_f$ (CHCl$_3$) 0.46; nmr 0.9 (3, broad t, J=6.0 Hz), 1.11 and 1.12 (3, each singlets), 1.0–1.9 (6, m), 5.75 (1, d, J=4.7 Hz), 7.5 (1, broad s) and 8.14 (1, broadened d, J=4.7 Hz); ir (film) 6.29, 5.95, 5.87, 3.48, 3.41, 3.37 and 3.22 to 2.78 (broad)$\mu$.

D. 4,4-Dimethyl-1-toluenesulfonyloxyoct-1-en-3-one (XXXII)

Unpurified XXXI (18.8 g, mmol) was dissolved in 190 ml of dry ether. This solution was stirred with ice-bath cooling under argon as 22 ml (158 mmol) of triethylamine was added in one portion followed by a solution of 24.3 g (128 mmol) of toluenesulfonyl chloride in 100 ml of dry ether which was added dropwise over 15 minutes. The resultant mixture was stirred with ice-bath cooling for 1.5 hours whereupon methanol (4 ml) was then added to the reaction mixture to quench excess toluenesulfonyl chloride. The resultant mixture was stirred another 8 minutes before it was washed sequentially with 10% aqueous hydrochloric acid, brine and then saturated aqueous sodium bicarbonate. The resultant solution was dried (MgSO$_4$) and then evaporated in vacuo to yield 40 g of residue containing XXXII. This residue was used without purification for the subsequent reaction, $R_f$(CHCl$_3$) 0.23 and 0.39 (cis and trans isomers); nmr 0.86 (3, broad t, J=6.0 Hz), 1.05 (6, s), 1.0–1.8 (6, m), 2.48 (3, s), 6.41 (1, d, J=11.8 Hz), 7.48 (2, d, J=8.5 Hz) 7.72 (1, d, J=11.8 Hz) and 7.93 (2, d, J=8.5 Hz).

E. 1-Iodo-4,4-dimethyloct-1E-en-3-one

The sample of XXXII prepared as described above was dissolved in 250 ml. of dry acetone and stirred overnight under argon with 25.2 g of sodium iodide and 1.0 g of lithium iodide. Tlc (CHCl$_3$) analysis of the reaction mixture (taken the next day) indicated that little or no reaction had taken place. A 0.25 ml portion of concentrated sulfuric acid was added to the dark colored reaction mixture and it was then heated to reflux using an oil bath whereupon the mixture rapidly became very viscous. Tlc analysis after a few minutes showed considerable amounts of XXXIII had formed at the expense of XXXII. After 14 hours reflux the resultant very dark colored reaction mixture was evaporated in vacuo. The residue was mixed with ether and washed with aqueous sodium thiosulfate and then saturated aqueous sodium bicarbonate. The resultant extract was dried (MgSO$_4$) and evaporated in vacuo to yield 18.7 g of XXXIII, bp 78°–88°, (0.2 mm); R$_f$(CHCl$_3$), 0.58 nmr 0.90 (3, broad t, J=6.0 Hz), 1.14 (6, s), 1.0–1.8 (6, m), 7.66 (1, d, J=14.8 Hz) and 8.07 (1, d, J=14.8 Hz); ir (film) 10.7, 9.64, 9.27, 6.80, 6.42, 5.92, 3.50, 3.41 and 3.38μ.

F. 1-Iodo-4,4-dimethyl-3RS-(1-ethoxyethoxy)-oct-1E-ene (XI-d)

Repeating in a similar manner the procedures of Example 9 I (above), but replacing XXVI with XXXIII yields 1-iodo-4,4-dimethyl-3RS-hydroxyoct-1E-ene which has the following properties: tlc (CHCl$_3$), R$_f$ 0.36; nmr (CDCl$_3$), 0.9, (9, m), 1.0–1.7 (6, m), 1.93 (1, s), 3.86 (1, d, J=6.0 Hz), 6.36 (1, d, J=14.0 Hz) and 6.77 ppm (1, d of d, J=14, 6 Hz); ir (film) 10.50, 9.80, 7.25, 6.82, 3.49, 3.42, 3.38 and 3.22–2.78μ.

Repeating in a similar manner the procedures of Example 9 J (above) but replacing XXVII with the above material yeilds XI-d which has the following spectra: Tlc (CHCl$_3$) R$_f$ 0.46 and 0.51 (diastereomer pair); nmr (0.7–1.9 (21, m), 3.4–3.9 (3, m), 4.70 (1, q, J=5.0 Hz), 6.23 (1, d, J=15 Hz) and 6.57 (1, d of d, J=15, 7 Hz).

EXAMPLE 15

Preparation of Ethyl 9α,11α,15R-trihydroxy-16,16-dimethylprosta-5Z,13E-dien-1-oate(16,16-Dimethyl-PGF$_{2α}$ ethyl ester, VIIg) and 9β,11α,15R-trihydroxy-16,16-dimethylprosta-5Z,13E-dien-1-oate (16,16-diemthyl-PGF$_{2β}$ ethyl ester, IX-b)

Repeating the procedure of Example 13 A above, except for replacing 1-iodo-1E-octene with XI-d affords VII-g as a clear oil, R$_f$(ethyl acetate) 0.32 and IX-b as a clear oil, R$_f$(ethyl acetate) 0.26.

EXAMPLE 16

Preparation of Ethyl 5, 9β-epoxy-11α,15R-dihydroxy-16,16-dimethylprost-13E-en-1-oate (VI-b, TR-7010)

Repeating the procedure of 10 B above, but replacing VII-b with IX-b and extending the initial reaction time to 18 hours (omitting the aqueous acid hydrolysis) affords VI-b as a clear oil, R$_f$ (ethyl acetate) 0.4; [α]$_D$+46.6°, (c 0.88, CHCl$_3$); ms m/e 392 (p-H$_2$), 347, (p-2H$_2$O), 348, 329, 311; nmr 0.85 (pair of s, 6), 1.26 (t, 3), 2.42 (broad t, 2), 4.20 (q, 2), 3.4–4.5 (complex, 4), 3.6 (m, 2); ir 2.78, 2.92 (broad), 5.75, 7.20, 9.10, 10.40μ.

EXAMPLE 17

Preparation of Ethyl 6, 9α-epoxy-11α,15R-dihydroxy-16,16-dimethylprost-13E-en-1-oate (V-g, TR-7006)

Repeating the procedure of Example 10 B above, except for replacing VII-b with VII-g (omitting the aqueous acid hydrolysis) affords V-g as a clear oil, R$_f$ (ethyl acetate) 0.36; [α]$_D$+30.6° (c 1.07, CHCl$_3$); nmr 0.86 (pair of s, 6) 1.22 (q, 3), 2.32 (broad t, 2) 4.18 (q, 2), 3.5–4.7 (complex, 4), 5.65 (m, 2); ir 2.75, 2.92 (broad), 5.75, 7.20, 10.40μ.

EXAMPLE 18

A. Evaluation of Inhibition of Human Platelet Aggregation by Analogues of Prostaglandins The ability of test compounds to inhibit platelet aggregation was determined by a modification of the turbidometric technique of Born (Nature, 194: 927 [1962]). Blood was collected from human volunteers who had not ingested aspirin or aspirin-containing products within the preceding two weeks in heparinized containers and was allowed to settle for one (1) hour. The platelet rich plasma (prp) supernates were collected and cooled. Siliconized glassware was used throughout.

In a representative assay 1.9 ml of prp and 0.2 ml of test compound at the appropriate concentrations (0.001 to 100 mcgm), or 0.2 ml of distilled water (control procedure) were placed in sample cuvettes. The cuvettes were placed in a 37° C. incubation block for 15 minutes, and then in a spectrophotometer linked to a strip chart recorder. After 30–60 seconds, 0.2 ml of a solution, prepared by diluting a calf-skin collagen solution 1:9 with Tyrodes' Solution, was added to each cuvette. Platelet aggregation was evidenced by a decrease in optical density.

Calculation of the degree of inhibition of platelet aggregation exhibited by each concentration of test compound was accomplished according to the method of Caprion et al., (Arzneim-Forch., 23: 1277 [1973]). An ED$_{50}$ value was then determined graphically. Activity of the compounds was scored as follows:

| ED$_{50}$ (mcg/kg) | Activity Value |
|---|---|
| No activity | 0 |
| >1.0 | 1 |
| >0.1 ≦1.0 | 2 |
| >0.01 ≦0.1 | 3 |
| >0.001 ≦0.01 | 4 |
| ≦0.001 | 5 |

B. Evaluation of the Effects of Prostaglandin Analogues on Gastric Secretion in the Rat A procedure based on that described by Lipmann (J. Pharm. Pharmacol., 21: 335 [1968]) was used to assess the influence of test compounds on gastric secretion. Rats of one sex weighing 150 to 200 g were randomly divided into groups of six animals each and fasted for 48 hours previously to the experiments, water being available ad libitum. The animals were anesthetized with ether, the abdomen was opened through a midline incision and the pylorus was ligated. Test compounds were diluted from stock solution so as to administer a dose of 1.5 mg/kg in a volume equivalent to 1 ml/kg. Subcutaneous injections were applied immediately after surgery and again 2 hours later, so that a total dose of 3.0 mg/kg was administered. Dilutions were made with phosphate buffer (pH 7.38), as recommended by Lee et al. (*Prostaglandins* 3: 29 [1973]), in order to insure adequate stability of drugs at the subcutaneous depot. Each compound was tested in one group of rats; an additional control group received only the vehicle.

Four hours after pyloric ligation the animals were killed with ether, the cardias ligated and stomachs removed. The volume of gastric secretion was measured and the contents centrifuged at 5000 rpm for 10 minutes. Total acid in the supernatant was titrated against a 0.1 N sodium hydroxide solution and the amount expressed in mEq.

Volume and total acid values of the treated group were compared with those of the controls by the "Squared" test. Antisecretory activity was scored according to the following scale:

| % decrease in acidity | Activity Value |
|---|---|
| <26 | 0 |
| 26–50, not significant | 1 |
| 26–50, significant | 2 |
| 51–75 | 3 |
| 76–100 | 4 |

TABLE F summarizes the results of the preceding assays utilizing preferred examples.

TABLE F

SUMMARY OF ACTIVITY OF PROSTAGLANDIN $I_2$ ANALOGUES IN: TEST A- INHIBITION OF HUMAN PLATELET AGGREGATION TEST B- INHIBITION OF RAT GASTRIC SECRETION

| TR NO. | Example No. | Activity Value Test A | Test B |
|---|---|---|---|
| 4811 | 1 | 1 | 0 |
| 4827 | 2 | 1 | 2 |
| 4913 | 4 | 2 | 2 |
| 4919 | 6 | 1 | 2 |
| 4914 | 7 | 1 | 0 |
| 4921 | 8 | 1 | 2 |
| 4937 | 9 | 1 | NT |
| 4965 | 10 | NT | 1 |
| 4970 | 11 | NT | 1 |
| 4973 | 12 | 1 | 0 |
| 7018 | 13 | 1 | 0 |
| 7010 | 16 | NT | 3 |
| 7006 | 17 | NT | 1 |

NT = not tested

What is claimed is:

1. A compound having the structural formula,

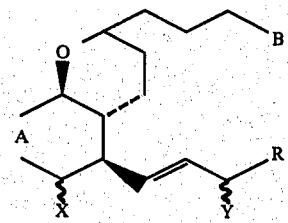

in which:
B is selected from the group consisting of $CH_2OH$ or COOT, where T is hydrogen, an alkyl group having from 1 to 3 carbon atoms or a pharmacologically acceptable cation;
A is selected from the group consisting of methylene or ethylene;
X and Y are selected from the group consisting of hydrogen or a hydroxyl group; and
R is selected from the group consisting of pentyl, cyclohexyl, bicyclo[3.2.0]hept-3-yl or 1,1-dimethylpentyl.

2. A compound according to claim 1 wherein the compound is ethyl 5,9β-epoxy-11α,15S-dihydroxyprost-13E-en-1-oate.

3. A compound according to claim 1 wherein the compound is 5,9β-epoxy-11α,15S-dihydroxyprost-13E-en-1-oic acid.

4. A compound according to claim 1 wherein the compound is ethyl 5,9β-epoxy-11α-hydroxyprost-13E-en-1-oate.

5. A compound according to claim 1 wherein the compound is ethyl 5,9β-epoxy-11α,15-dihydroxy-16,20-methanoprost-13E-en-1-oate.

6. A compound according to claim 1 wherein the compound is ethyl 5,9β-epoxy-11α,15R-dihydroxy-16,16-dimethylprost-13E-en-1-oate.

* * * * *

UNITED STATES PATENT AND TRADEMARK OFFICE
CERTIFICATE OF CORRECTION

PATENT NO. : 4,206,127
DATED : June 3, 1980
INVENTOR(S) : Warren D. Woessner

It is certified that error appears in the above-identified patent and that said Letters Patent are hereby corrected as shown below:

| | | |
|---|---|---|
| Column 3, | Line 62; | place a -- V -- beneath the formula appearing at Lines 53-61 of said column. |
| Column 4, | Line 62; | place a -- VI -- beneath the formula appearing at Lines 53-61 of said column. |
| Column 5, | Lines 40-43; | delete the formula and insert -- 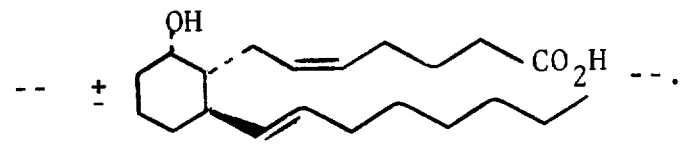 --. |
| Column 5, | Lines 44-47 | delete the formula and insert -- 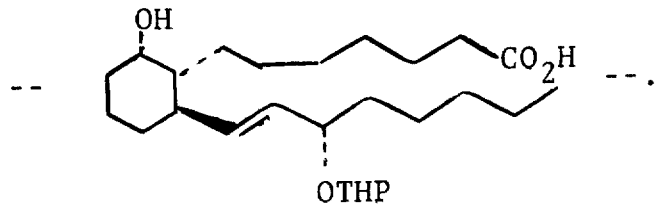 --. |

UNITED STATES PATENT AND TRADEMARK OFFICE
CERTIFICATE OF CORRECTION

PATENT NO. : 4,206,127
DATED : June 3, 1980
INVENTOR(S) : Warren D. Woessner

It is certified that error appears in the above-identified patent and that said Letters Patent are hereby corrected as shown below:

| | | |
|---|---|---|
| Column 9, | Line 45; | place the designation -- XIV -- beneath the first formula. |
| Column 12, | Line 15; | change "Z'-" to -- Z'= --. |
| Column 23, | Line 42; | change "ciomplex" to -- complex --. |
| Column 25, | Line 14; | change "11=" to -- 11α --. |
| Column 26, | Line 15; | change "CA" to -- ca --. |
| Column 29, | Line 19; | change "Squared" to |

Signed and Sealed this

Fifth Day of August 1980

[SEAL]

Attest:

Attesting Officer

SIDNEY A. DIAMOND

Commissioner of Patents and Trademarks